(12) United States Patent
Forsell (10) Patent No.: US 9,320,909 B2
(45) Date of Patent: Apr. 26, 2016

(54) ACCESSORY FOR AN IMPLANT

(76) Inventor: Peter Forsell, Bouveret (CH)

( * ) Notice: Subject to any disclaimer, the term of this patent is extended or adjusted under 35 U.S.C. 154(b) by 25 days.

(21) Appl. No.: 13/123,192

(22) PCT Filed: Oct. 12, 2009

(86) PCT No.: PCT/SE2009/051160
§ 371 (c)(1),
(2), (4) Date: Apr. 7, 2011

(87) PCT Pub. No.: WO2010/042067
PCT Pub. Date: Apr. 15, 2010

(65) Prior Publication Data
US 2011/0195666 A1  Aug. 11, 2011

Related U.S. Application Data (60) Provisional application No. 61/227,534, filed on Jul. 22, 2009.

(30) Foreign Application Priority Data

Oct. 10, 2008 (SE) ..................................... 0802149

(51) Int. Cl.
| | | |
|---|---|---|
| *H04B 5/00* | (2006.01) | |
| *A61N 1/372* | (2006.01) | |
| *A61B 5/00* | (2006.01) | |
| *A61N 1/378* | (2006.01) | |
| *G06F 19/00* | (2011.01) | |
| *A61B 5/06* | (2006.01) | |
| *A61F 2/00* | (2006.01) | |

(52) U.S. Cl.
CPC .......... *A61N 1/37264* (2013.01); *A61B 5/0031* (2013.01); *A61N 1/3787* (2013.01); *G06F 19/3412* (2013.01); *A61B 5/06* (2013.01); *A61B 2560/0214* (2013.01); *A61F 2/0004* (2013.01)

(58) Field of Classification Search
CPC ..................................................... H04B 5/0037
USPC ....................................... 455/41.1, 41.2, 41.3
See application file for complete search history.

(56) References Cited

U.S. PATENT DOCUMENTS

| | | |
|---|---|---|
| 4,134,408 A | 1/1979 | Brownlee et al. |
| 5,690,693 A | 11/1997 | Wang et al. |
| 5,713,939 A | 2/1998 | Nedungadi et al. |
| 6,456,883 B1 | 9/2002 | Torgerson et al. |

(Continued)

OTHER PUBLICATIONS

International Search Report for for PCT/SE2009/051160, mailed Nov. 24, 2009.

(Continued)

*Primary Examiner* — Wen Huang (57) ABSTRACT

An accessory (11) for use with an implanted medical device (100, 102) in a mammal body is intended for use externally to said mammal body and is arranged to wirelessly transmit signals to said implanted medical device (100,102). Said signals are sent in order to initiate a backup function or a backup system in said implanted medical device. The signals can be sent to initiate said backup function or backup system to override a built in control and/or powering system of the implanted device (100, 102). Also, the accessory can send said signals as wireless power signals to a receiver (102) for wirelessly receiving power in said implanted medical device, the signal information regarding the backup function being coded into said power signals.

20 Claims, 2 Drawing Sheets

(56) References Cited

U.S. PATENT DOCUMENTS

| | | |
|---|---|---|
| 6,553,263 B1 | 4/2003 | Meadows et al. |
| 6,879,859 B1* | 4/2005 | Boveja .................... 607/45 |
| 2002/0128690 A1* | 9/2002 | Zarinetchi et al. ............ 607/33 |
| 2002/0140399 A1* | 10/2002 | Echarri et al. .............. 320/130 |
| 2005/0004621 A1 | 1/2005 | Boveja et al. |
| 2008/0214888 A1* | 9/2008 | Ben Shalom ................ 600/17 |
| 2009/0011706 A1* | 1/2009 | Wilson et al. ............... 455/41.1 |

OTHER PUBLICATIONS

Written Opinion of the International Searching Authority for PCT/SE2009/051160, mailed Nov. 24, 2009.

Extended European Search Report in EP patent application No. 09819521.7 (Foresell) dated Mar. 16, 2012.

* cited by examiner

ACCESSORY FOR AN IMPLANT

This application is the U.S. national phase of International Application No. PCT/SE2009/051160, filed 12 Oct. 2009, which designated the U.S. and claims priority to SE Application No. 0802149-5, filed 10 Oct. 2008, and the benefit of U.S. Provisional No. 61/227,534 filed 22 Jul. 2009, the entire contents of each of which are hereby incorporated by reference.

RELATED APPLICATIONS

This application claims priority and benefit from Swedish patent application No. 0802149-5, filed Oct. 10, 2008 and U.S. provisional patent application No. 61/227,534, filed Jul. 22, 2009, the entire teachings of which are incorporated herein by reference. This application has some material in common with the simultaneously filed International patent applications also having the title "Charger for implant" and claiming priority from (Coupling) Swedish patent application No. 0802147-9, filed Oct. 10, 2008 and U.S. provisional patent application No. 61/213,223, filed May 19, 2009, from (RFID) Swedish patent application No. 0802148-7, filed Oct. 10, 2008 and U.S. provisional patent application No. 61/213,209, filed May 18, 2009, from (Switching) Swedish patent application No. 0802155-2, filed Oct. 10, 2008 and U.S. provisional patent application No. 61/213,225, filed May 19, 2009, and from (Passive) Swedish patent application No. 0802145-3, filed Oct. 10, 2008 and U.S. provisional patent application No. 61/213,224, filed May 19, 2009, respectively, the entire teachings of which are also incorporated herein by reference.

TECHNICAL FIELD

The present invention relates to an accessory for use with an implanted medical device in a mammal body, as well as to a power source arranged to be implanted in a mammal patient's body for supplying power to such an implanted medical device.

BACKGROUND

Medical devices which are implanted in a mammal body, such as the human body, can be used to replace or supplement a large variety of bodily functions or organs.

Since it usually is difficult or uncomfortable to access a device which has been implanted in a mammal body, such devices are usually arranged to use a power source which supplies the implanted device with power in a wireless fashion, either in order to power the device directly, or in order to charge a rechargeable energy source such as an electrochemical cell or battery in the device.

In a medical device which is implanted in a mammal body, the function of the device is naturally of paramount importance. If an implanted device malfunctions, it is desirable for the user of the device, or somebody in their immediate vicinity, to be capable of overcoming such a malfunction, at least until the user has received proper help from medical professionals.

Methods and devices for charging a rechargeable energy source are e.g. disclosed in the published U.S. patent application 2005/0075697 and U.S. Pat. Nos. 5,690,693, 5,702,431, 5,713,939 and 6,456,883.

SUMMARY

As explained above, there is thus a need for a user of an implanted medical device which has malfunctioned to be capable of restarting the device in a proper way, or to at least achieve some degree of function or functionality in the device.

This need is addressed by the present invention in that it discloses an accessory for use with an implanted medical device in a mammal body, with the accessory being intended for use external to the mammal body and being arranged to wirelessly transmit signals to the implanted medical device.

Thus, the signals are sent from the accessory in order to initiate a backup function or a backup system in the implanted device.

Thus, a user or, for example, a family member, who has detected a malfunction in an implanted medical device can use the accessory to overcome the malfunction, and to reestablish normal function, or a degree of such a function, to the implanted medical device.

For example, if the implanted medical device is used to constrict the urethra of a patient having urinary incontinence, the user must naturally be capable of opening said constriction, in order to perform urination, with the opening suitably being done by remote control.

If the user, or, for example, a caretaker of the user, notices that it is not possible to urinate using the implanted device and an accompanying, generally remote, control, the accessory can be used in order to accomplish the opening of the urethra and the subsequent urination. In fact, the accessory may in some embodiments itself be part of the remote control.

In one embodiment, the accessory is arranged to wirelessly send its signals as power signals to a receiver for providing power in the medical implant, including information regarding the backup function being coded into said power signals.

The accessory may be used either as a "back-up" device for an ordinary device for communicating with and powering an implanted medical device, or it may be used as an emergency system to override functions in the implant in order to accomplish a function of the implant, such as, in the example above, the opening of the urethra.

Naturally, the application with the urethra described above is only an example of one of many possible applications of the accessory, the example being intended to illustrate the general concept. The accessory can be used for a variety of different medical implants in order to perform many different functions and is not limited to act on restriction devices only.

In one embodiment, the signals from the accessory are sent to initiate said backup function or backup system in order to override a built in control and/or powering system of the implanted device.

In one embodiment, the accessory is arranged to send its signals wirelessly as information signals, and the accessory is then also arranged to wirelessly transmit power to the medical implant in order to power the operation of the backup function in the implant.

In one embodiment, the accessory is arranged to wirelessly receive signals from the implant and to use those received signals to determine whether the accessory should send further signals and/or energy to the implant.

In one embodiment, the accessory further comprises a first power source arranged to wirelessly supply power to a second power source in the implanted medical device in order to energize or charge the second power source, and the first power source comprises a first coil through which energy can be passed in order to be supplied to the second energy source, i.e. that of the implanted device.

Also generally, a power source can be arranged to be implanted in a mammal patient's body for supplying power to an implanted medical device in the mammal's body. This power source comprises a receiver for wirelessly receiving power from a power source external to the patient's body, said receiver comprising a coil.

The accessory may comprise a system including an external control unit for controlling predefined functions of said medical device, and adapted to send overriding control and power signals, related to lack of feed-back signals from the medical device or lack of functionality of the medical device, and wherein said signals are sent in order to initiate said backup system to override a built in control and/or powering system of the implanted device (100, 102).

The alternative may include a system, wherein the external control unit is adapted to send predefined information and the medical device adapted to receive said predefined information and together adapted to cause a replacement of the medical device normal communication or powering system, wherein powering is over-rid from an external power supply controlled by said external control unit for sending wireless energy and wherein said medical device is adapted to perform a predefined powered emergency action.

The accessory may comprise a system including an external control unit for controlling predefined functions of said medical device, and adapted to send overriding control and power signals, related to lack of feed-back signals from the medical device or lack of functionality of the medical device, and wherein said signals are sent in order to initiate said backup system to override a built in control and/or powering system of the implanted device (100, 102).

The system may further comprise a system, wherein the external control unit is adapted to send predefined information and the medical device adapted to receive said predefined information and together adapted to cause a replacement of the medical device normal communication or powering system, wherein powering is over-rid from an external power supply controlled by said external control unit for sending wireless energy and wherein said medical device is adapted to perform a predefined powered emergency action.

The medical device is adapted to make a replacement of the feed-back information system and adapted to send feed-back from a override communication system relating to energy supply and command action.

Additional objects and advantages of the invention will be set forth in the description which follows, and in part will be obvious from the description, or may be learned by practice of the invention. The objects and advantages of the invention may be realized and obtained by means of the methods, processes, instrumentalities and combinations particularly pointed out in the appended claims.

BRIEF DESCRIPTION OF THE DRAWINGS

While the novel features of the invention are set forth with particularly in the appended claims, a complete understanding of the invention, both as to organization and content, and of the above and other features thereof may be gained from and the invention will be better appreciated from a consideration of the following detailed description of non-limiting embodiments presented hereinbelow with reference to the accompanying drawings, in which:

DETAILED DESCRIPTION

A system, devices therefor and a method will now be described which are intended for use with a medical device which has been, or is intended to be, implanted in a mammal body, such as the human body.

The nature of the implanted medical device may vary. Examples include implanted artificial constriction devices on bodily organs or on artificial, e.g. implanted, organs such as the sphincter, the urethra or an intestine. An accessory for use with such an implanted device is provided, and also a power source for supplying power to such an implanted device, as will be described below, as well as a system comprising both the accessory and the power supply.

A generic medical implant and its interaction with an external device will first be briefly explained with reference to the block diagram of FIG. 1.

Figure 1:
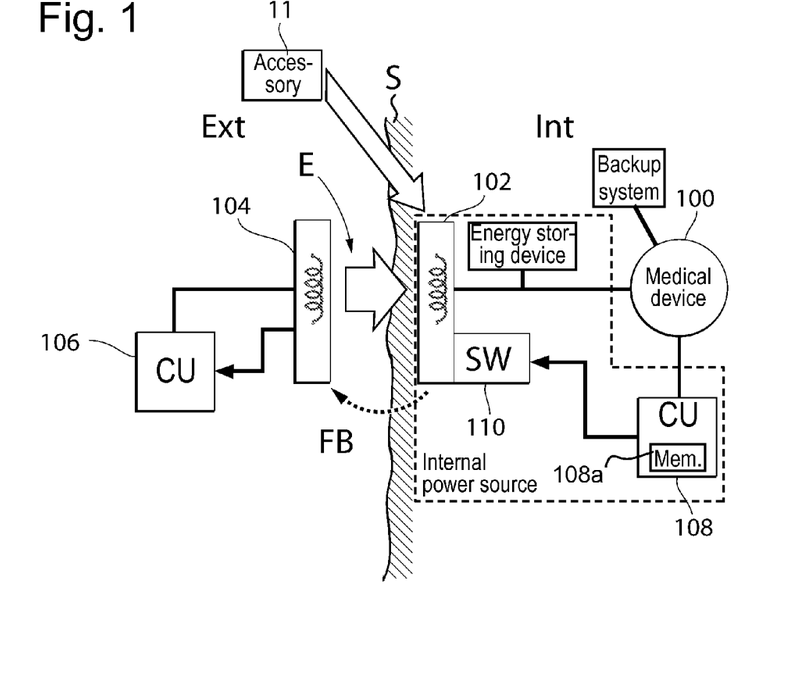
FIG. 1 is a block diagram of an implanted device illustrating the interaction thereof with an external device.

Thus, the block diagram of FIG. 1 schematically illustrates an arrangement for supplying an accurate amount of energy to an electrically operable medical device 100 implanted in a patient, whose skin is indicated by a vertical line S separating the interior "Int" of the patient from the exterior "Ext". The medical device 100 is connected to an internal energy receiver 102, likewise located inside the patient, such as just beneath the skin S. Generally speaking, the energy receiver 102 may be placed in the abdomen, thorax, muscle fascia, e.g. in the abdominal wall, subcutaneously, or at any other suitable location. The energy receiver 102 is arranged to wirelessly receive energy E transmitted from an external energy source 104 located outside the skin S, suitably in the vicinity of the energy receiver 102.

The energy E is wirelessly transferred using a first or primary coil, not shown, arranged in the energy source 104 and an adjacent second or secondary coil, not shown, arranged in the energy receiver 102. When an electrical current is made to flown in the primary coil, a voltage is induced in the secondary coil, which can cause an electric current to flow therein, the electric current representing energy and can be used to operate the medical device 100, e.g. after storing the energy in an energy storing device or accumulator, such as a battery or a capacitor, not shown.

The internal energy receiver 102 is arranged to transfer suitable feedback control information FB from the secondary coil to the primary coil by switching the secondary coil on and off to induce a detectable impedance load variation in the primary coil. This load variation is created and controlled to encode the feedback control information in a useful manner. The feedback control information thus communicated from the energy receiver 102 to the energy source 104 generally relates to the energy for operating the medical device 100. The feedback control information is then used for controlling the wireless transmission of energy from the external energy source 104. The amount of transferred energy is regulated by an external control unit 106 controlling the energy source 104.

Thus, the energy supply arrangement illustrated in FIG. 1 may operate substantially in the following manner, in the case where the wireless transmission of energy is controlled based on the energy balance described above.

The energy balance may first be determined by the internal control unit 108. Feedback control information FB relating to the energy is also created by the internal control unit 108, and the feedback control information FB is transmitted from the energy receiver 102 to the energy source 104. Alternatively, the energy balance can instead be determined by the external control unit 106, depending on the implementation, as mentioned above. In that case, the feedback control information FB may carry measurement results from various sensors, not shown. The amount of energy emitted from the energy source 104 can then be regulated by the external control unit 106, based on the determined energy balance, e.g. in response to the received feedback control information FB. This process may be repeated intermittently at certain intervals during ongoing energy transfer, or may be executed on a more or less continuous basis during the energy transfer.

Also shown schematically in FIG. 1 is an accessory 11. The accessory 11 is shown as being a separate unit distinct from the "regular" external energy supply arrangement 104, 105, but may also be integrated in such a device.

As explained previously, the accessory is arranged to wirelessly transmit signals to said implanted medical device, the transmitted signals being sent in order to initiate a backup function or a backup system in said device.

The backup system or function is not illustrated in FIG. 1, but may be seen as being integrated into one or more of the implanted device or devices 100, 102, 108, although the backup system may also be a separate implanted device connected to one or more of the implanted devices 100, 102, 108.

The accessory 11 is thus used when a user or a caretaker of the user notices that the implanted device 100 is not functioning properly, in which case the accessory 11 is used to trigger a backup function or a backup system in the device 100.

In one embodiment, the signals which are transmitted by the accessory 11 are transmitted to initiate the backup function or backup system in order to make them override a built in control and/or powering system of the implanted device, i.e. to override the function of the control unit 108 and/or the energy receiver 102.

In one embodiment, the signals from the accessory 100 are wirelessly sent as power signals to a receiver for wirelessly powering said device, information regarding the backup function being coded into said power signals. This receiver can be the ordinary power receiver 102, or an auxiliary power receiver, not shown, or alternatively, a receiver, not shown, for radio signals, which will trigger the backup function.

Alternatively, since the malfunction of the medical device can be caused either by a power failure or by some other malfunction, the accessory 11 will wirelessly send its signals as information signals, i.e. as radio signals, while also, or alternately, wirelessly sending power to the device 100 via the device 102, in order to power the operation of the backup function in the device.

Figure 2:
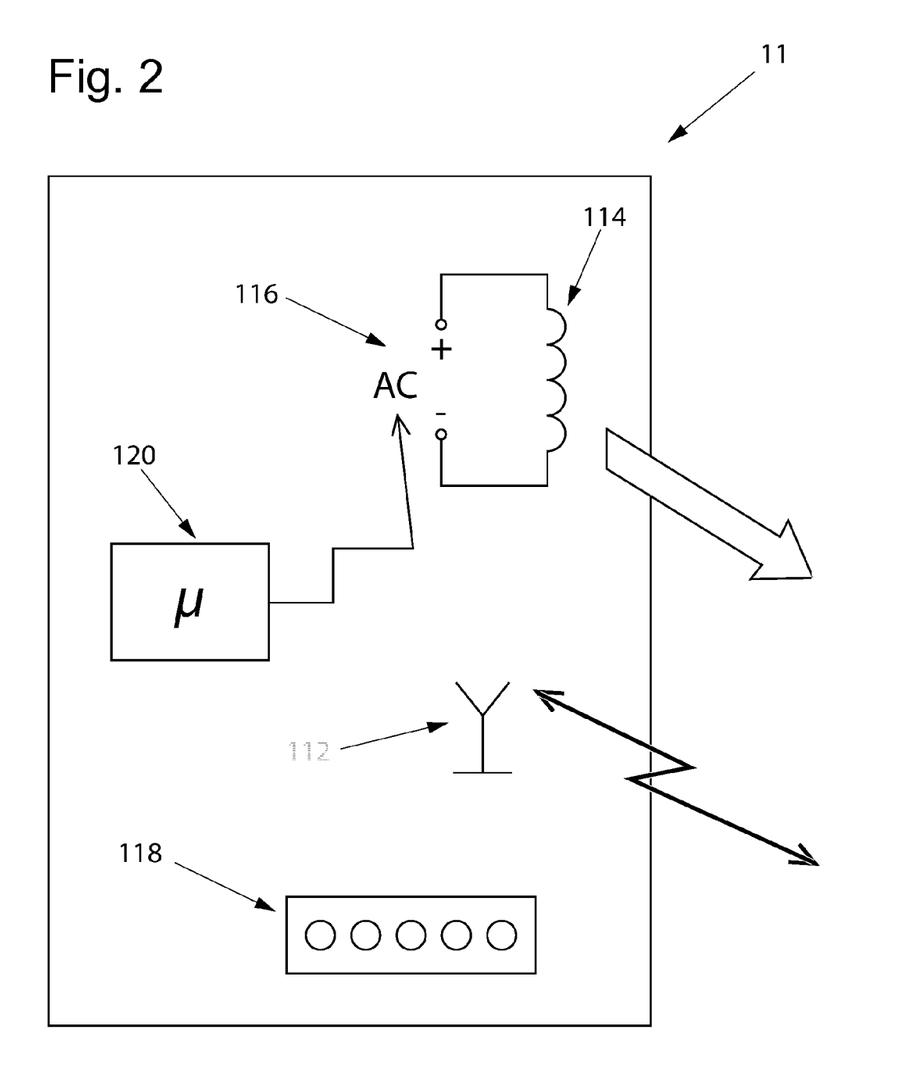
FIG. 2 is a block diagram of an accessory for an implanted device.

The structure of the accessory 11 is shown schematically in FIG. 2 as comprising a radio transmitter or transceiver 112, a first coil 114, and a power supply 116 for making AC power flow through the first coil 114.

In order to allow the accessory 11 or the user of the accessory 11 to ascertain if the medical device has resumed proper function, the accessory is in one embodiment arranged to wirelessly receive signals from the implanted device 100, and will use these received signals in order to determine whether the accessory should send further signals and/or energy to the device. The contents of such feedback information from the implant 100 can be presented to the user on a display 118 of the accessory 11.

Thus, as seen in FIG. 2, the accessory 11 may comprise a first power source which is arranged to wirelessly supply power to a second power source in the implanted medical device in order to energize or charge the second power source. The first power source may in one embodiment comprise the first coil 114 through which an electric current can be made to flow by the AC source 116, in order to be supplied to the second energy source, i.e. that of the implanted device 100.

Since the accessory 11 will be used externally to the implant 100, it is useful for the user of the accessory to know where to position the accessory 11 in order to achieve an optimal effect of the signals, i.e. the information signals and/or the energy which are/is sent. In order to accomplish a good positioning of the accessory 11, the accessory is equipped to detect such a position.

The "position detecting" of the accessory is suitably accomplished by means of making the power source of the accessory be capable of detecting impedance variations when being moved in relation to the implanted device, in order to optimize the position of the accessory with respect to the position of the internal energy receiver 102 or the second power source, i.e. the power source of the implanted device 100.

As mentioned above, the optimization is made in order to optimize the supply of energy or information signals between the first and the second power sources. It will described below how impedance variations can be accomplished such as by operating a switch. The impedance variations which are detected can e.g. be an impedance maximum and/or an impedance minimum as the accessory is being moved over the patient's skin "S". Since the impedance of a primary coil in a transformer circuit is changed when its electromagnetic coupling to the secondary coil varies, impedance variations that may relatively small can also be detected when the primary coil is moved in relation to the secondary coil, as long as the secondary coil allows an electric current to flow therein. Thus, in the latter case no active switching for the secondary coil is required.

In the switching case, the electric current flowing in the coil in the internal energy receiver 102 is shut off and on, this causing an impedance variation of an external coil in the accessory. The impedance variation can e.g. be detected by determining the intensity or amplitude of the electric current flowing through the coil of the accessory that acts as the primary coil in a transformer circuit having the coil in the internal energy receiver as the secondary coil. Characteristics of the electric current flowing through the primary coil when moving the accessory 11 can be sensed.

The switching of the electric current in the coil in the internal energy receiver 102 on and of can in this case be made using a switch, as will described below, so that the electric circuit including the coil is controlled to be closed or open according to any suitable pattern, such as for example periodically, e.g. the times when electric current is allowed to flow in the coil can occur in a regularly repeated pattern and the times when no electric current is allowed to flow in the coil can occur in a regularly repeated pattern, the patterns having the same repetition frequency. In an alternative the times when the electric current starts to be allow to flow in the coil and the times when the electric current starts not to be allow to flow in the coil can occur at random, by closing and opening a switch at random times. The latter control pattern can be made in order not to interfere with other electronic components.

The impedance variation is generally detected or received as a variation between two levels, a maximum level and a minimum level. The variation, i.e. the distance between the two extreme levels, then represents or indicates the electromagnetic coupling between the primary coil and the secondary coil in the transformer circuit. When the coil of the accessory 11 is being moved in relation to the coil of the internal energy source, the moving of the external power supply results in a variation of the distance or difference between the two levels depending on the position of the external coil in relation to the internal coil. The feedback information such as the impedance variation or some quantity derived therefrom can as described above be used to generate a signal and/or indications to a user. Thus, in some cases e.g. only one of the maximum and minimum values of the sensed impedance can be used. Such indications can then include that it is indicated whether the value of the variation, during the moving of the external power supply, is increasing or decreasing, an increasing value indicating a higher or better electromagnetic coupling or a lower or worse electromagnetic coupling.

The position of the first power source, i.e. the power source of the accessory, which is optimized with respect to the second power source, i.e. the power source of the implanted device, can thus be searched for and detected. In such an optimized position the distance between the two power sources is usually minimized, at least "electrically" if not geometrically, and allows the best possible position for the wireless transfer of energy.

In order for the user to be capable of detecting an optimal position for the accessory, the accessory may comprise, as shown in FIG. 2, an indicator which indicates how good a certain position is for the accessory, said indication then being made in response to said impedance variation. The indicator can, as indicated in FIG. 2, comprise a display 118 which is arranged to display the feedback information such as the variation of the impedance or some quantity derived therefrom.

Turning now to the feedback information, the feedback information can of course also be transferred as radio signals from a transmitter in or adjacent to the implanted device, this case illustrated by the arrow from the transmitter 112 in this case being a double arrow.

In one embodiment, the accessory 11 can, e.g. in an initial state before starting to move the accessory to find an optimal position, calibrate the supply of energy to the second power source by increasing the amount of transferred energy to the second power source until a change of said impedance variation is detected, the change then being different from zero or the absolute value of the change being in excess of a predefined threshold, i.e. the impedance variation exceeds or falls below certain threshold values. The calibration can be carried out commanded by a control unit 120 in the accessory 11, comprising a controller such as a microprocessor.

The control unit 120 can also in one embodiment comprise an analyzing unit, not shown, for analyzing the detected impedance variations and for indicating an optimal placement of the second coil or of the accessory in relation to said implanted device or said second coil, based on the analyzed impedance variations. The analyzing unit can be part of the control unit 120, but can also be separate from therefrom.

As mentioned above, also a power source can be provided which is arranged to be implanted in a mammal patient's body for supplying power to an implanted medical device in the mammal's body. Such a power source may be a part of the power source or internal power receiver 102 of FIG. 1, or it may be a separate unit. It will here be described with reference to the power source 102 in FIG. 1.

The internal power source 102 comprises a receiver for wirelessly receiving power from a power source external to the patient's body, this receiver comprising a coil, not shown, which will be a second or secondary coil, if the coil 114 of the accessory 11 is seen as the primary or first coil.

In one embodiment, the internal power source 102 also includes a backup override system, not shown, which is arranged to receive signals, for example from the accessory 11, in order to trigger the backup system to override one or more other functions for controlling and/or powering the medical device 100. Thus, the internal power source can also, together with the backup or override system, replace a malfunctioning "main" system in the implanted device 110. A system which can be overridden is for example the power system of the implanted device, or the "main function" of the device 100.

The internal power source 102 may also, in some embodiments, additionally comprise a power switch to switch the second coil on and off from connection with the implanted medical device 100. If this switching off and on of the coil is done in order to communicate with an external device such as the accessory 11, the switching is suitably carried out using a control unit, not shown, comprised in the power source and arranged to make and control transmissions of feedback information to an external power source such as the accessory 11, this information in one embodiment being related to the power received from the external power supply, and the transmission being made as impedance variations caused by switching said switch on and off in a predetermined pattern.

As is obvious from the description above, the internal power source 102 can be arranged to use the accessory 11, in any of its embodiments, as an external power supply.

Turning now to the backup system which can be comprised in the internal power source 102, this backup system is in one embodiment arranged to perform an emergency activity which comprises a predetermined activity in the implanted medical device 100. This predetermined activity can be chosen from a wide range of activities, depending on the nature of the medical device, but in one embodiment, the predetermined activity comprises running a motor or pumping using a pump or stimulating using a stimulator.

Suitably, the predetermined activity is arranged to use the energy that is wirelessly supplied from an external source such as the accessory 11.

As is obvious from the description above, the feedback information from the power source is created by an internal control unit 108 switching a power switch 110 on and off, suitably in order to create a pattern of digital pulses of varied impedance load which will be detectable by an external power source.

In one embodiment, the feedback information comprises information on a predetermined variable parameter which is related to the wirelessly received energy in the medical implant.

Also, the internal power source 102 is in one embodiment, in performing the predetermined emergency activity, arranged to wirelessly receive said energy in varied amounts, based on the feedback information.

Returning to the predetermined emergency activity, this may comprise one or more of the following:
1. Opening an artificial restriction device on a bodily organ such as the sphincter, the urethra or an intestine.
2. Opening an artificial restriction device on an artificial bodily organ such as an artificial sphincter, an artificial urethra or an artificial intestine.
3. Releasing a pharmaceutical drug within the mammal body.
4. Emptying a luminal organ within said body.

The accessory 11 can be arranged to use the internal power source 102 as at least part of the implanted device 100 for which the accessory is intended.

The accessory 11 and the power source 102 together form a system for providing additional security to an implanted medical device 100.

As described above, an internal control unit 108 may be implanted in the patient and connected to the medical device 100. The internal control unit 108 is used to control the on and off switching of the secondary coil. The feedback control information FB may include at least one predetermined parameter relating to the received energy. When using the internal control unit 108, the feedback control information may relate to the received energy and may also require artificial intelligence to be generated.

The on and off switching of the secondary coil may be executed by means of an implantable switch 110 (SW) at the energy receiver 102 as illustrated in FIG. 1. The switch is connected to and controlled by the internal control unit 108. The switch may be an electronic switch such as a transistor. Furthermore, the internal control unit may comprise a memory 108a for storing the transferred feedback control information FB.

The energy balance mentioned above may be determined by the internal control unit 108. The feedback control information can then relate to the determined energy balance. In that case, the external control unit 106 may be used to control the wireless transmission of energy E from the external energy source 104 based on the determined energy balance and using the received feedback control information FB.

Alternatively, the external control unit 106 may be used to determine the energy balance, based on the feedback control information FB which in that case comprises measurements relating to characteristics of the medical device 100. The external control unit 106 is then further used to control the wireless transmission of energy from the external energy source 104 based on the determined energy balance and using the received feedback control information FB.

The internal control unit 108 may be arranged to receive various measurements obtained from suitable sensors or the like, not shown, measuring certain characteristics of the medical device 100, somehow reflecting the energy needed for proper operation of the medical device 100. Moreover, the current condition of the patient may also be detected by means of suitable measuring devices or sensors, in order to provide parameters reflecting the patient's condition. Hence, such characteristics and/or parameters may be related to the current state of the medical device 100, such as power consumption, operational mode and temperature, as well as the patient's condition reflected by e.g. body temperature, blood pressure, heartbeat rate and breathing.

Furthermore, an energy storing device or accumulator, not shown here, may also be connected to the energy receiver 102 for accumulating received energy for later use by the medical device 100. Alternatively or additionally, characteristics of such an energy storing device, also relating to the energy, may be measured as well. The energy storing device may be an electrochemical cell or a battery, and the measured characteristics may be related to the current state of the battery, such as voltage, temperature, etc. In order to provide sufficient voltage and electric current to the medical device 100, and also to avoid excessive heating, it is clearly understood that the battery should be charged optimally by receiving a correct amount of energy from the energy receiver 102, i.e. not too little or too much. The energy storing device may also be a capacitor having corresponding characteristics.

For example, battery characteristics may be measured on a regular basis to determine the current state of the battery, which then may be stored as state information in a suitable storage means in the internal control unit 108. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 108 may be arranged to determine the energy balance and/or the currently required amount of energy, either energy per time unit or accumulated energy, based on measurements made by the above mentioned sensors or measuring devices on the medical device 100, or the patient, or an energy storing device if used, or any combination thereof. The amount of energy transmitted from the energy source 104 may then be regulated in response to the received feedback control information.

Alternatively, sensor measurements can be transmitted to the external control unit 106 wherein the energy balance and/or the currently required amount of energy can be determined by the external control unit 106, thus basically integrating the function described above of the internal control unit 108 in the external control unit 106. In that case, the internal control unit 108 can be omitted and the sensor measurements are comprised in the feedback control information FB. The energy balance and the currently required amount of energy can then be determined by the external control unit 106 based on those sensor measurements.

Hence, the system as described herein employs the feedback of information indicating the required energy, which may in many cases be more efficient than in other systems because it is based on the actual use of energy that is compared to the received energy, e.g. with respect to the amount of energy, the energy difference, or the energy receiving rate as compared to the energy rate used by the medical device. The medical device may use the received energy either for consuming or for storing the energy in an energy storage device or the like. The different parameters discussed above would thus be used if relevant and needed and then as a tool for determining the actual energy balance. However, such parameters may also be needed per se for any actions taken internally to specifically operate the medical device 100.

The feedback control information FB may further be modulated with respect to frequency, phase or amplitude.

The amount of transferred energy can generally be regulated by adjusting various transmission parameters in the energy source 104, such as voltage, current, amplitude, wave frequency and pulse characteristics.

Figure 3:
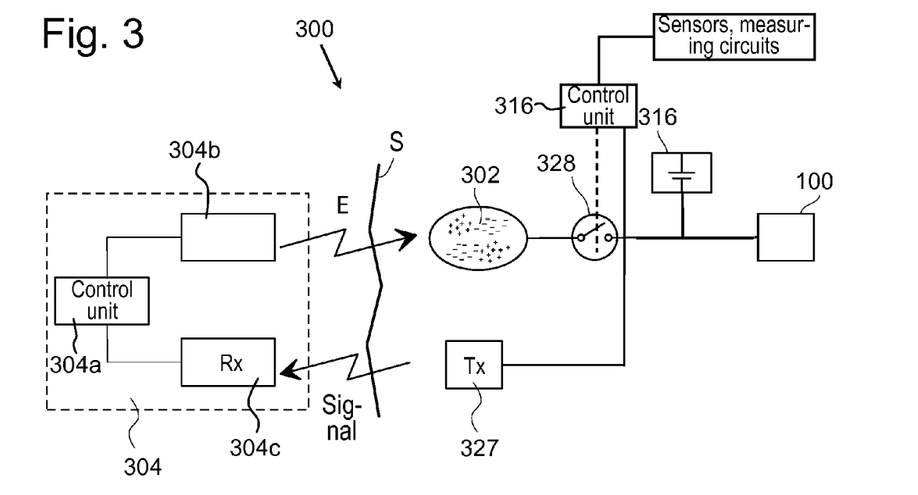
FIG. 3 is a schematic of a system including an implanted device and an accessory.

FIG. 3 is a schematic of a system 300 for supply of power. Here, the internal energy receiver comprises an energy-transforming device 302, which can correspond to or be part of the energy receiver 102 described above, located inside the patient's body such as just beneath the patient's skin S.

Generally, the implanted energy-transforming device 302 may be placed in the abdomen, thorax, muscle fascia, e.g. in the abdominal wall, subcutaneously, or at any other suitable location. The implanted energy-transforming device 302 is arranged to receive energy E wirelessly transmitted from the external energy source 304a, arranged in an external energy transmission device 304, which can correspond to or be part of the external energy source 104 described above and can be located outside the patient's skin S in the vicinity of the implanted energy-transforming device 302.

As is well known in the art, the wirelessly transferred energy E may generally be transferred by means of any suitable Transcutaneous Energy Transfer (TET) device, such as a device including a primary coil, not shown, arranged in the external energy source 304a and an adjacent secondary coil, not shown, arranged in the implanted energy-transforming device 302. When an electric current is made to flow through the primary coil, a voltage is induced in the secondary coil which can be used drive an electric current to power the energy consuming components of the implanted device 100, e.g. after storing the incoming energy in an implanted energy source, such as a rechargeable electrochemical cell or battery or a capacitor. However, the general aspect of the system and method as described herein is are not limited to any particular energy transfer technique, TET devices or energy sources, and wirelessly transmitted energy of any suitable kind may be used.

The amount of energy received by the implanted energy receiver 102 (302) may be compared to the energy used by the components of the implanted device 100. The term "energy used" is then understood to include also energy stored by or in implanted components of the apparatus. A control device includes an external control unit 304b that controls the external energy source 304a based on the determined energy balance to regulate the amount of transferred energy. In order to transfer the correct amount of energy, the energy balance and the required amount of energy is determined by a determination device including an implanted internal control unit 315, that can be part of or correspond to the unit 108 described above and is connected between the switch 326, that can be part of or correspond to the switch 110 described above, and the medical device 100.

The internal control unit 315 may thus be arranged to receive various measurements obtained by suitable sensors or the like, not shown, measuring certain characteristics of the medical device 100, somehow reflecting the required amount of energy needed for proper operation of the medical device 100. Moreover, the current condition of the patient may also be detected by means of suitable measuring devices or sensors, in order to provide parameters reflecting the patient's condition. Hence, such characteristics and/or parameters may be related to the current state of the medical device 100, such as power consumption, operational mode and temperature, as well as the patient's condition reflected by parameters such as body temperature, blood pressure, heartbeat rate and breathing. Physical parameters of the patient of other kinds and functional parameters of the device of other kinds are described elsewhere.

Furthermore, an energy source such as an accumulator 316 may optionally be connected to the implanted energy-transforming device 302 for accumulating received energy for later use by the medical device 100. Alternatively or additionally, characteristics of such an accumulator, also reflecting the required amount of energy, may be measured as well. The accumulator may be replaced by a rechargeable electrochemical cell or battery, and the measured characteristics may be related to the current state of the cell or battery, any electrical parameter such as energy consumption voltage, temperature, etc. In order to provide sufficient voltage and electric current to the medical device 100, and also to avoid excessive heating, it is clearly understood that the cell or battery should be charged optimally by receiving a correct amount of energy from the implanted energy-transforming device 302, i.e. not too little or too much. The accumulator may also be a capacitor having corresponding characteristics.

For example, battery characteristics may be measured on a regular basis to determine the current state of the battery, which then may be stored as state information in a suitable storage unit, not shown, in the internal control unit 315. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 315 of the determination device is arranged to determine the energy balance and/or the currently required amount of energy, either energy per time unit or accumulated energy, based on measurements made by the above mentioned sensors or measuring devices of the medical device 100, or the patient, or an implanted energy source if used, or any combination thereof. The internal control unit 315 is further connected to an internal signal transmitter 327, arranged to transmit a control signal reflecting the determined required amount of energy, to an external signal receiver 304c connected to the external control unit 304b. The amount of energy transmitted from the external energy source 304a may then be regulated in response to the received control signal.

Alternatively, the determination device may include the external control unit 304b. In this alternative, sensor measurements can be transmitted directly to the external control unit 304b wherein the energy balance and/or the currently required amount of energy can be determined by the external control unit 304b, thus integrating the above described function of the internal control unit 315 in the external control unit 304b. In that case, the internal control unit 315 can be omitted and the sensor measurements are supplied directly to the internal signal transmitter 327 which sends information of the measurements to the external signal receiver 304c and the external control unit 304b. The energy balance and the currently required amount of energy can then be determined by the external control unit 304b based on those sensor measurements.

Hence, the system of FIG. 3 employs the feedback of information indicating the required energy, which at least in some cases can be more efficient than in other systems because it is based on the actual use of energy that is compared to the received energy, e.g. with respect to the amount of energy, the energy difference, or the energy receiving rate as compared to the energy rate used by implanted energy consuming components of the apparatus. The system may use the received energy either for consuming or for storing it in an implanted energy source or the like such as the accumulator 316. The different parameters discussed above would thus be used if relevant and needed and then as a tool for determining the actual energy balance. However, such parameters may also be needed per se for any actions taken internally to specifically operate the medical device.

The internal signal transmitter 327 and the external signal receiver 304c may be implemented as separate units using suitable signal transfer means, such as radio, IR (Infrared) or ultrasonic signals. Alternatively, the internal signal transmitter 327 and the external signal receiver 304c may be integrated in the implanted energy-transforming device 302 and the external energy source 304a, respectively, so as to convey control signals in a reverse direction relative to the energy transfer, basically using the same transmission technique. The control signals may be modulated with respect to frequency, phase or amplitude.

Thus, the feedback information may be transferred either by a separate communication system including receivers and transmitters or may be integrated in the energy system. Such an integrated information feedback and energy system can comprise an implantable internal energy receiver 102 for wirelessly receiving energy, the energy receiver having an internal first coil and a first electronic circuit connected to the first coil, and an external energy transmitter such the unit 104 or 304b for wirelessly transmitting energy, the energy transmitter having an external second coil and a second electronic circuit connected to the second coil. The external second coil of the energy transmitter wirelessly transmits energy which is received by the first coil of the energy receiver. This system further comprises a power switch such as the items illustrated at 110 and 328 for switching the connection of the internal first coil to the first electronic circuit on and off, such that feedback information related to the charging of the first coil is received by the external energy transmitter as an impedance variation the external second coil, when the power switch switches the connection of the internal first coil to the first electronic circuit on and off. In implementing the of FIG. 3, the switch 326 is either separate and controlled by the internal control unit 315, or integrated in the internal control unit 315. It should be understood that the switch 326 should be interpreted in its broadest embodiment. This means that it can be a transistor, MCU, MCPU, ASIC FPGA or a DA converter or any other electronic component or circuit that may switch the power on and off.

To conclude, the energy supply system illustrated in FIG. 3 may operate basically in the following manner. The energy balance is first determined by the internal control unit 315 of the determination device. A control signal reflecting the required amount of energy is also created by the internal control unit 315, and the control signal is transmitted from the internal signal transmitter 327 to the external signal receiver 304c. Alternatively, the energy balance can be determined by the external control unit 304b instead depending on the implementation, as mentioned above. In that case, the control signal may carry measurement results from various sensors. The amount of energy emitted from the external energy source 304a can then be regulated by the external control unit 304b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 304a, such as voltage, current, amplitude, wave frequency and pulse characteristics.

The system may also be used to obtain information about the coupling factor between the coils in a TET system such as for calibrating the system to find an optimal place for the external coil in relation to the internal coil and to optimize energy transfer. The amount of transmitted energy can be compared to the amount of received energy. If for example the external coil is moved, the coupling factor may vary and correctly preformed movements could bring the external coil to the optimal place for energy transfer. The external coil can be arranged to calibrate the amount of transferred energy to achieve the feedback information in the determination device, before the coupling factor is maximized.

The coupling factor information may also be used as a feedback during energy transfer. In such a case, the energy supply system comprises an implantable internal energy receiver for wirelessly receiving energy, the energy receiver having an internal first coil and a first electronic circuit connected to the first coil, and an external energy transmitter for wirelessly transmitting energy, the energy transmitter having an external second coil and a second electronic circuit connected to the second coil. The external second coil of the energy transmitter wirelessly transmits energy which is received by the first coil of the energy receiver. The system further comprises a feedback device for communicating the amount of energy received in the first coil as a feedback information, and the second electronic circuit can include a determination device for receiving the feedback information and for comparing the amount of energy transmitted from the second coil with feedback information related to the amount of energy received in the first coil to obtain the coupling factor between the first coil and the second coil. The energy transmitter may regulate the transmitted energy in response to the obtained coupling factor.

A method of implanting an implant can comprise the steps of:
cutting the skin,
placing said medical device or at least the internal parts of the energy supply system inside the body, and
suturing and closing the skin.

The system can then perform the following steps:
when receiving a specific command including a wirelessly transmitted energy field, sending predetermined feedback information out of the body, such information having at least one variable parameter, said feedback being sent as detectable impedance variations from a coil being switched on and off by a power switch such as the switch 328 or 110, and
communicating digital information related to an amount of received energy, simultaneously performing a predetermined emergency activity when wirelessly receiving energy.

In operating the implanted device, the emergency activity can comprise at least one of:
1. opening a restriction device, such as an artificial urinary sphincter or intestinal sphincter,
2. emptying a luminal organ within the body, such as a urine bladder,
3. delivering a drug from a drug delivery device, and
4. stimulating a part of the body by a stimulation device.

While specific embodiments of the invention have been illustrated and described herein, it is realized that numerous other embodiments may be envisaged and that numerous additional advantages, modifications and changes will readily occur to those skilled in the art without departing from the spirit and scope of the invention. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents. It is therefore to be understood that the appended claims are intended to cover all such modifications and changes as fall within a true spirit and scope of the invention. Numerous other embodiments may be envisaged without departing from the spirit and scope of the invention.

The invention claimed is:

1. An internal power source adapted to be implanted in a mammal patient's body for supplying power to an implanted medical device in the mammal's body, the internal power source comprising a receiver adapted to wirelessly receive power from a first external power source external to the patient's body, when and if the implanted medical device is malfunctioning, said receiver comprising:
a coil, and
a backup system arranged to receive external signals comprising information adapted to initiate a re-start of the mal-functioning medical device, and which trigger the backup system to override one or more other functions for controlling and powering said medical device, to at least achieve some degree of functionality in the malfunctioning implanted medical device,
said backup system being arranged to perform an emergency activity, said activity comprising a predetermined activity in the implanted medical device comprising at least one of: running a motor and pumping using a pump, and
said backup system being further arranged to use the wirelessly transferred energy for performing said predetermined activity.

2. The internal power source of claim 1, wherein the backup system is adapted to override at least one of: a malfunctioning power system of the implanted device, and the main function of the device.

3. The internal power source of claim 1, wherein the receiver comprises a power switch to switch said coil on and off from connection with said implanted medical device.

4. The internal power source of claim 1, further comprising a control unit which is arranged to make and control transmissions of feedback information to the first external power source, said information being related to the power received from the first external power supply.

5. The internal power source according to claim 4, wherein the feedback information comprises information on a predetermined variable parameter which is related to the wirelessly received energy in the medical implant.

6. The internal power source according to claim 5, adapted to wirelessly receive said energy in varied amounts, based on the feedback information.

7. The internal power source according to claim 5, when receiving a specific command includes receiving a wirelessly transmitted energy field adapted to operate the medical device by:
   sending a predetermined feedback information out from the body, such information having at least one variable parameter,
   communicating digital information related to an amount of received energy, and
   performing a predetermined emergency activity simultaneously as the receiving of said wirelessly transmitted energy.

8. The internal power source according to claim 4, comprising an internal control unit and a power switch, wherein the feedback information is created by the internal control unit controlling the power switch and thereby switching the power switch on and off for creating a pattern of digital pulses of varied impedance load arranged to be detectable by the first external power source.

9. The internal power source of claim 1, wherein the internal power source is adapted to use an accessory, placed external to the patient's body, including the first external power source.

10. The internal power source according to claim 1, wherein the accessory is adapted to:
    in response to the malfunctioning of the medical device, being caused by a power failure, to wirelessly send power to the medical device, in order to power the operation of the backup function in the device, or
    in response to the malfunctioning of the medical device, being a malfunction other than power failure, wirelessly send both information signals and power to the medical device, in order to power the operation of the backup function in the device.

11. The internal power source according to claim 1, wherein the predetermined activity comprises at least one of:
    the opening of an artificial restriction device on a bodily organ, such as a sphincter, a urethra or an intestine,
    the closing of an artificial restriction device on an artificial bodily organ, such as an artificial sphincter, an artificial urethra or an artificial intestine,
    releasing a pharmaceutical drug within the patient's body,
    emptying a luminal organ within the patient's body,
    emptying a urine bladder, and
    stimulating a part of the patient's body.

12. The internal power source according to claim 1 further comprising an accessory for use external to the patient's body and adapted for wirelessly transmitting signals to said implanted medical device, the signals being adapted to be sent in order to initiate a backup function or a backup system in said implanted medical device to override a built in control and powering system of the implanted device, wherein the accessory is arranged to send said signals as power signals wirelessly to a receiver, for wirelessly receiving power in said implanted medical device, wherein said signals comprises information regarding the backup function being coded into said power signals,
    wherein the receiver of the power source comprises a coil, and
    said medical device backup system of the power source is adapted to perform said predetermined activity comprising at least one of:
    running a motor, and
    pumping a fluid.

13. The internal power source according to claim 12, wherein the accessory is arranged to at least one of:
    send signals as wirelessly transmitted information signals,
    wirelessly transmit power to said device, in order to power the operation of the backup function in the implanted medical device,
    wirelessly receive signals from said implanted medical device,
    using said received signals to determine whether the accessory should send further signals, or energy or signals and energy to the implanted medical device.

14. The internal power source according to claim 12, wherein the first external power source is arranged to wirelessly supply power to the internal power source in the implanted medical device to energize or charge said internal power source, the first external power source comprising a first coil through which energy can be passed to be supplied to the internal energy source in the implanted device.

15. The internal power source according to claim 14, wherein the first external power source is arranged to detect impedance variations when moved in relation to the implanted device, in order to optimize the position of the accessory with respect to the position of the internal power source of the implanted device, said optimization being for the supply of energy and for transferring information signals between the first external and the internal power source, said impedance variation being an impedance maximum or minimum.

16. The internal power source according to claim 15, wherein the position of the first external power source is optimized with respect to the internal power source.

17. The internal power source according to claim 15, wherein the first external power source comprises an analyzing unit arranged to:
    analyze detected impedance variations, and
    indicate an optimal placement of said second coil or of the accessory in relation to said implanted device or said second coil based on the analyzed impedance variations.

18. The internal power source according to claim 14, wherein the first external power source is arranged to calibrate the supply of energy to the internal power source by increasing the amount of transferred energy to the internal power source until a change is detected, said change being in excess of or below a predefined threshold.

19. The internal power source according to claim 12 further comprising an indicator arranged to indicate a better position for supplying energy to the internal power source.

20. The internal power source according to claim 19, wherein said indicator comprises a display arranged to display the feedback information.

* * * * *